United States Patent
Abichandani et al.

(10) Patent No.: US 6,670,517 B1
(45) Date of Patent: Dec. 30, 2003

(54) PROCESS FOR ALKYLATING AROMATICS (75) Inventors: Jeevan Sahib Abichandani, Houston, TX (US); Chaya Rao Venkat, Sedona, AZ (US); Dominick Nicholas Mazzone, Wenonah, NJ (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/644,999

(22) Filed: Aug. 24, 2000

(51) Int. Cl.[7] .................................................. C07C 2/66
(52) U.S. Cl. ........................ 585/467; 585/446; 585/323
(58) Field of Search ................................. 585/446, 467, 585/323

(56) References Cited

U.S. PATENT DOCUMENTS

| | | | |
|---|---|---|---|
| 3,293,192 A | 12/1966 | Maher et al. ................ 252/430 |
| 3,308,069 A | 3/1967 | Wadlinger et al. .......... 252/455 |
| 3,442,795 A | 5/1969 | Kerr et al. ................... 208/120 |
| 3,449,070 A | 6/1969 | McDaniel et al. ............ 23/111 |
| 3,702,886 A | 11/1972 | Argauer et al. .............. 423/328 |
| 3,709,979 A | 1/1973 | Pochen Chu ................. 423/328 |
| 3,751,504 A | 8/1973 | Keown et al. ............... 260/672 |
| 3,751,506 A | 8/1973 | Burress ....................... 260/671 |
| 3,832,449 A | 8/1974 | Rosinski et al. ............. 423/328 |
| RE28,341 E | 2/1975 | Wadlinger et al. .......... 208/120 |
| 3,923,636 A | 12/1975 | Mead et al. ................... 208/58 |
| 3,926,782 A * | 12/1975 | Plank et al. ................. 208/135 |
| 3,972,983 A | 8/1976 | Ciric .......................... 423/328 |
| 4,016,218 A | 4/1977 | Haag et al. .................. 260/671 |
| 4,016,245 A | 4/1977 | Plank et al. ................. 423/328 |
| 4,060,568 A | 11/1977 | Rodewald .................... 260/682 |
| 4,076,842 A | 2/1978 | Plank et al. ................. 423/328 |
| 4,086,287 A | 4/1978 | Kaeding et al. ............. 260/671 |
| 4,117,026 A | 9/1978 | Haag et al. .................. 260/671 |
| RE29,948 E | 3/1979 | Dwyer et al. ................ 208/110 |
| 4,169,111 A | 9/1979 | Wight ......................... 585/323 |
| 4,234,231 A | 11/1980 | Yan ................................. 299/4 |
| 4,401,556 A | 8/1983 | Bezman et al. .............. 208/111 |
| 4,418,235 A * | 11/1983 | Haag et al. .................. 585/407 |
| 4,439,409 A | 3/1984 | Puppe et al. ................. 423/328 |
| 4,556,477 A | 12/1985 | Dwyer ......................... 208/111 |
| 4,950,823 A * | 8/1990 | Harandi et al. .............. 585/322 |
| 4,992,606 A | 2/1991 | Kushnerick et al. ......... 585/467 |
| 5,077,445 A | 12/1991 | Le ............................... 585/467 |
| 5,149,894 A | 9/1992 | Holtermann et al. ........ 585/467 |
| 5,157,185 A * | 10/1992 | Chu et al. .................... 585/467 |
| 5,236,575 A | 8/1993 | Bennett et al. ................ 208/46 |
| 5,240,892 A | 8/1993 | Klocke ........................ 502/77 |
| 5,243,117 A | 9/1993 | Chang et al. ............... 585/467 |
| 5,250,277 A | 10/1993 | Kresge et al. ............. 423/329.1 |
| 5,258,565 A | 11/1993 | Kresge et al. .............. 585/467 |
| 5,292,698 A | 3/1994 | Chu et al. ..................... 502/84 |
| 5,334,795 A | 8/1994 | Chu et al. .................... 585/467 |
| 5,362,697 A | 11/1994 | Fung et al. ................... 502/71 |
| 5,369,071 A | 11/1994 | Degnan et al. ............... 502/71 |
| 5,371,310 A | 12/1994 | Bennett et al. .............. 585/467 |
| 5,453,554 A | 9/1995 | Cheng et al. ................ 585/467 |
| 5,493,065 A | 2/1996 | Cheng et al. ................ 585/467 |
| 5,530,170 A | 6/1996 | Beck et al. .................. 588/467 |
| 5,557,024 A | 9/1996 | Cheng et al. ................ 585/467 |
| 5,689,027 A | 11/1997 | Abichandani et al. ....... 585/481 |

FOREIGN PATENT DOCUMENTS

WO    WO-95/01318 A1 *  1/1995

\* cited by examiner

*Primary Examiner*—Walter D. Griffin (57) ABSTRACT

A process for alkylating aromatics is provided which comprises contacting an aromatic-containing feed with alkylating agent in the presence of a silica-bound ZSM-5 zeolite catalyst, wherein the ZSM-5 has a crystal size no greater than 0.05 micron, said contacting being conducted under alkylating conditions to provide a product containing a monoalkylated aromatic fraction and a polyalkylated aromatic fraction, wherein the polyalkylated aromatic fraction contains at least 40 wt. % of the para-dialkylaromatic species. The polyalkylated aromatic fraction may be contacted with unsubstituted aromatic and a transalkylation catalyst under transalkylating conditions to provide a monoalkylated aromatic-rich stream, e.g., an ethylbenzene-rich stream.

20 Claims, 4 Drawing Sheets figure 3 figure 4

PROCESS FOR ALKYLATING AROMATICS

FIELD OF THE INVENTION

The present invention relates to a process for alkylating aromatics.

BACKGROUND OF THE INVENTION

The present invention is directed to a process for aromatics alkylation and in particular the alkylation of benzene with ethylene to provide ethylbenzene. Existing processes for producing ethylbenzene inherently produce polyalkylated species as well as the desired monoalkyated product. It is therefore normal to transalkylate the polyalkylated species with benzene to produce additional ethylbenzene either by recycling the polyalkylated species to the alkylation reactor or by feeding the polyalkylated species to a separate transalkylation reactor. It is, however, found that para-diethylbenzene (p-DEB) is easier to transalkylate than the ortho and meta isomers. There is therefore a continuing need for an aromatics alkylation process in which the polyalkylated by-products are rich in the para dialkyl component. Such a process would be particularly useful where it employs a catalyst which exhibits both alkylation and transalkylation activity under similar operating conditions inasmuch as the alkylation and transalkylation steps could be carried out in a single reactor with recycle of diethylbenzene.

U.S. Pat. No. 3,751,504 to Keown et al. and U.S. Pat. No. 3,751,506 to Burress describe vapor phase alkylation of aromatic hydrocarbons with olefins, e.g., benzene with ethylene, in the presence of ZSM-5 zeolite.

U.S. Pat. No. 4,086,287 to Kaeding et al. discloses a method for selectively ethylating monoalkyl benzenes to para-dialkyl substituted benzenes, such as para-diethylbenzene using ethylene as alkylating agent, over a zeolite-containing catalyst, e.g., ZSM-5, which may be incorporated in a matrix such as clay, silica, and/or metal oxides. The zeolite may be modified by incorporating a difficultly reducible oxide such as oxides of phosphorus, boron, and/or magnesium.

U.S. Pat. No. 4,117,026 to Haag et al. discloses a method for selectively producing para-dialkyl substituted benzenes from monoalkyl substituted benzenes, e.g., toluene and $C_2$–$C_{15}$ olefin, over a zeolite-containing catalyst, e.g., ZSM-5, which may be incorporated in a matrix such as clay, silica, and/or metal oxides. The reference further teaches enhanced para-xylene selectivity with large crystal ZSM-5 (1 micron) compared to small crystal ZSM-5 (0.03 micron).

U.S. Pat. No. 4,169,111 to Wight teaches a method for producing ethylbenzene by alkylating benzene with ethylene in the presence of a catalyst, e.g., ZSM-5 which can be bound with mineral oxide binder, e.g., alumina gel or silica gel. The process produces ethylbenzene and polyethylbenzenes. At least a portion of diethylbenzene fraction is recycled to the alkylation zone, while the remainder thereof plus the higher polyethylbenzenes are transalkylated with benzene to produce additional ethylbenzene.

U.S. Pat. No. 5,243,117 to Chang et al. discloses a method for selectively producing para-dialkyl substituted benzenes using a silica-modified non-organic ZSM-5 catalyst treated with an organosilicon compound, e.g., phenylmethylsilicone. The catalyst may be silica-bound.

U.S. Pat. No. 5,530,170 to Beck et al. discloses a method for alkylating ethylbenzene with ethylene to selectively produce para-diethylbenzene using a ZSM-5 zeolite catalyst which has been selectivated by multiple treatments with a siliceous material, e.g., dimethylsilicone. The catalyst may be silica-bound.

U.S. Pat. No. 5,689,027 to Abichandani et al. discloses a method for converting ethylbenzene to compounds that may be removed from an aromatic hydrocarbon stream with minimal xylene loss using a silica bound intermediate pore size zeolite that has been selectivated.

SUMMARY OF THE INVENTION

According to the invention it has now been found that a silica bound, small crystal ZSM-5 zeolite catalyst provides a higher p-DEB content in total DEB when used in the ethylation of benzene, thereby facilitating subsequent DEB conversion to ethylbenzene (EB). The novel catalyst also allows reduced alkylation temperature and lower xylene make as compared to conventional catalysts.

In one aspect, the present invention relates to a process for alkylating aromatics which comprises contacting an aromatic-containing feed with alkylating agent in the presence of a silica-bound ZSM-5 zeolite catalyst, wherein the ZSM-5 has a crystal size no greater than 0.05 micron, e.g., 0.02 to 0.05 micron, said contacting being conducted under alkylating conditions to provide a product containing a monoalkylated aromatic fraction and a polyalkylated aromatic fraction, wherein the polyalkylated aromatic fraction contains at least 40 wt. % of the para-dialkylaromatic species.

In another aspect, the present invention relates to a process for preparing a monoalkylated aromatic compound which comprises:

i) contacting an aromatic-containing feed in an alkylating reactor with alkylating agent in the presence of a silica-bound ZSM-5 zeolite alkylation catalyst, wherein the ZSM-5 has a crystal size of no greater than 0.05 micron, e.g., 0.02 to 0.05 micron, said contacting being conducted under alkylating conditions to provide a product containing a monoalkylated aromatic fraction and a polyalkylated aromatic fraction, wherein the polyalkylated aromatic fraction contains at least 40 wt % of the paradialkylaromatic species;

ii) separating the polyalkylated aromatic fraction from the product, and iii) contacting the polyalkylated aromatic fraction in the presence of unsubstituted aromatic and a transalkylation catalyst under transalkylating conditions to provide a monoalkylated aromatic-rich stream, e.g., an ethylbenzene-rich stream.

The reference in the present specification to the ZSM-5 having a "crystal size" of no greater than 0.05 micron is used to mean that the maximum dimension of the crystals in any direction is no greater than 0.05 micron.

The above and other objects, features and advantages of the present invention will be better understood from the following detailed descriptions, taken in conjunction with the accompanying drawings, all of which are given by illustration only, and are not limitative of the present invention.

DETAILED DESCRIPTION OF THE INVENTION

The present invention is directed to a process for producing a monoalkylated aromatic compound, particularly ethylbenzene, by reacting an aromatic feedstock, particularly benzene, with alkylating agent, particularly ethylene, in the presence of a silica-bound ZSM-5 zeolite alkylation catalyst, wherein the ZSM-5 has a crystal size of no greater than, 0.05 micron, e.g., 0.02 to 0.05 micron. Preferably, the catalyst contains at least 70 wt. % zeolite. The resultant product contains both the desired monoalkylated aromatic compound and polyalkylated aromatic compounds rich in the para-dialkylaromatic species. The polyalkylated aromatic compounds are separated from the alkylation product and reacted with further aromatic feedstock in the presence of a transalkylation catalyst to produce additional monoalkylated product.

Alkylation and Transalkylation Catalysts

The alkylation catalyst used in the present invention comprises the zeolite ZSM-5 having a crystal size (maximum dimension in any direction) of no greater than 0.05 micron, e.g., about 0.02 to about 0.05 micron. ZSM-5 is disclosed in U.S. Pat. No. 3,702,886 and U.S. Pat. Reissue No. 29,948 and a process for making small crystal ZSM-5 is disclosed in U.S. Pat. No. 4,060,568, U.S. Pat. No. 5,240,892 and U.S. Pat. No. 5,369,071. The zeolite is composited with a silica binder, preferably such that the alkylation catalyst contains at least 70 wt. % zeolite, more preferably 70–90 wt. %, and most preferably 75–85 wt. % zeolite, for example about 80 wt. % zeolite. The ZSM-5 employed preferably has a $SiO_2/Al_2O_3$ molar ratio greater than 40, more preferably from 60 to 80, and most preferably about 70.

Although it is known that zeolite catalysts can be selectivated by treatment with selectivating agents such as coke or organosilicon compounds, it is preferred that the alkylation catalysts employed in the present invention not be so treated. In particular, it is preferred that the ZSM-5 catalyst employed in the alkylation step of the invention has a Diffusion Parameter, $D/(r^2 \times 10^6)$, for 2,2-dimethylbutane of at least 500, and more preferably from 700 to 2000, when measured at a temperature of 120° C. and a 2,2-dimethylbutane pressure of 60 torr (8 kPa), wherein D is the diffusion coefficient ($cm^2/sec$) and r is the crystal radius (cm). The required Diffusion Parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1957.

The transalkylation catalyst used in the process of the invention is preferably ZSM-5 and most preferably the same silica-bound, small crystal ZSM-5 used as the alkylation catalyst. Alternative transalkylation catalysts include other medium pore zeolites having a Constraint Index of 2–12 (as defined in U.S. Pat. No. 4,016,218), such as ZSM-11, ZSM-12, ZSM-22, ZSM-23, ZSM-35, and ZSM-48. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

In addition, large-pore zeolites, including those zeolites having a Constraint Index less than 2, are suitable for use as the transalkylation catalyst in the process of the invention. Suitable large pore zeolites include zeolite Beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556.

Other acidic solid oxides, which may be used to catalyze the present transalkylation reaction, include MCM-22, PSH-3, SSZ-25, MCM-36, MCM-49 and MCM-56. MCM-22 and its use to catalyze the synthesis of alkylaromatics, including ethylbenzene, is described in U.S. Pat. Nos. 4,992,606; 5,077,445; and 5,334,795. PSH-3 is described in U.S Pat. No. 4,439,409. SSZ-25 and its use in aromatics alkylation are described in U.S. Pat. No. 5,149,894. MCM-36 is described in U.S. Pat. Nos. 5,250,277 and 5,292,698. U.S. Pat. No. 5,258,565 describes the synthesis of alkylaromatics, including ethylbenzene, using a catalyst comprising MCM-36. MCM-49 is described in U.S Pat. No. 5,236,575. The use of MCM-49 to catalyze the synthesis of alkylaromatics, including ethylbenzene, is described in U.S. Pat. Nos. 5,493,065 and 5,371,310. MCM-56 is described in U.S. Pat. No. 5,362,697. The use of MCM-56 to catalyze the synthesis of alkylaromatics including ethylbenzene is described in U.S. Pat. Nos. 5,557,024 and 5,453,554.

Reactants

The reactants used in the process of the invention include an alkylatable aromatic compound and an alkylating agent.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which can be present as substituents on the aromatic compound contain from about 1 to 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes make in such instances may be less than about 500 ppm.

Reformate containing substantial quantities of benzene, toluene and/or xylene constitutes a particularly useful feed for the alkylation process of this invention.

The alkylating agents useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |

-continued

|  | Wt. % | Mole % |
| --- | --- | --- |
| Isobutane | 12.9 | 10.3 |
| n-Butane | 3.3 | 2.6 |
| Butenes | 22.1 | 18.32 |
| Pentanes | 0.7 | 0.4 |

Preferably, the reactants in the process of the invention are benzene and ethylene and the desired reaction product is ethylbenzene.

Reaction Conditions

The alkylation and transalkylation reactions may take place under liquid phase conditions or vapor phase conditions or mixed liquid/vapor phase conditions. For example, one of these reactions may take place under liquid phase or mixed liquid/vapor phase conditions, while the other reaction takes place under vapor phase conditions. However, both reactions preferably take place under vapor phase conditions.

Particular conditions for carrying out the vapor phase alkylation of benzene with ethylene may include a temperature of from about 650 to 900° F. (343 to 482° C.), e.g., from about 700 to 850° F. (371 to 454° C.), a pressure of about atmospheric to about 3000 psig, e.g., from about 25 psig to about 450 psig, a WHSV based on ethylene of from about 0.5 to about 10.0 $hr^{-1}$, e.g., about 0.5 to about 2.0 $hr^{-1}$ and a mole ratio of benzene to ethylene of from 1:1 to 30:1.

Liquid phase alkylation of benzene with ethylene may be carried out at temperatures between 300 and 650° F. (150 to 340° C.) usually in the range of 400 to 520° F. (205 to 270° C). Pressures during the liquid phase alkylation of benzene with ethylene may be as high as about 3000 psig (20875 kPa) although generally will not exceed 1000 psig (7000 kPa). The reaction may be carried out in the absence of hydrogen and accordingly the prevailing pressures are those of the reactant species. The space velocity may be from about 0.1 to 20 WHSV, based on the ethylene feed. Preferred space velocities for the liquid phase alkylation of benzene with ethylene include ranges, for example, from about 0.5 to about 3 WHSV, e.g., from about 0.75 to 2.0 WHSV, (ethylene). The ratio of the benzene to the ethylene in the alkylation reactor may be from 1:1 to 30:1 molar, normally about 5:1 to 20:1 molar, and in most cases from about 5:1 to 10:1 molar.

Particular conditions for carrying out the vapor phase transalkylation of benzene with polyethylbenzenes may include a temperature of from about 260° C. to about 482° C., e.g., from about 370 to 450° C., a pressure of from about atmospheric to about 3000 psig, e.g., from about 50 to about 500 psig, a WHSV based on the weight of the total vapor feed to the reaction zone of from about 1 to about 50 $hr^{-1}$ and a mole ratio of benzene to polyethylbenzene of from about 1 to about 50.

Particular conditions for carrying out the liquid phase transalkylation of benzene with polyethylbenzenes may include a temperature of from about 150° C. to about 260° C., a pressure of 7000 kPa or less, a WHSV based on the weight of the total liquid feed to the reaction zone of from about 0.5 to about 2.0 $hr^{-1}$ and a mole ratio of benzene to polyethylbenzene of from 1:1 to 30:1.

The process of the present invention, which employs silica-bound ZSM-5 zeolite catalyst composite of no greater than 0.05 micron, e.g., 0.02–0.05 micron, zeolite crystal size, as the alkylation catalyst, provides certain advantages over prior art processes. In particular, the polyalkylated fraction of the alkylation product contains at least 40 wt. % of the para-dialkylaromatic species. Moreover, the para-diethylbenzene content of the alkylation product is greater than 45 wt. %, preferably greater than 50 wt. % of the total diethylbenzene in the product. The high para-diethylbenzene content facilitates subsequent transalkylation.

The alkylation step of the process of the invention may be effected at a start of cycle temperature 20–30° F. lower, e.g., well below 750° F., than conventional vapor phase EB processes possibly owing to enhanced coke resistance of the silica-bound catalyst as compared to comparable alumina-bound catalyst composite. The lower start of cycle temperature provides longer cycle lengths.

Moreover, the silica-bound ZSM-5 used as the alkylation catalyst in the process of the invention provides lower xylene make, with the xylene content of the alkylation product typically being no greater than 900 ppmw, preferably no greater than 800 ppmw. In particular, the process of the present invention can provide ethylene conversion of at least 96 wt %, preferably at least 96.5 wt% and less than 800 ppmw xylenes/EB, preferably less than 750 ppmw xylenes/EB, after 4 days on stream at ethylene WHSV of 4, aromatics/ethylene ratio of 50 and inlet temperatures of 750° F. Furthermore, residue production can be limited by using the present process which can provide an ethylbenzene-rich product stream containing no greater than 0.4 wt. %, preferably no greater than 0.3, wt. % $C_{11+}$residue.

In one embodiment of the invention, the polyalkylating and transalkylating steps can be carried out in a single reactor preferably using the same catalyst bed by recycling polyalkylated aromatic products, e.g., a para-diethylbenzene-rich stream, back to the alkylating reactor. Such a procedure is especially useful wherein the ZSM-5 catalyst composite employed exhibits both alkylation and transalkylation activity. Alternatively, the transalkylating step can be carried out in a transalkylating reactor separate from the alkylating reactor. In such instances each reactor may employ the same or different catalyst composites in their respective catalyst beds. A particularly preferred embodiment employs an alkylating and/or transalkylating reactor having four to six catalyst beds.

The following examples will serve to further illustrate processes and some advantages of the present invention.

EXAMPLE 1

PREPARATION OF ZSM-5 Catalysis

Silica Bound ZSM-5 Catalyst

A silica bound catalyst of the present invention was formulated by the following procedure: 178 parts of a small crystal ZSM-5 (0.02–0.05 micron size) drycake was added to a muller mixer along with 22 parts of a precipitated silica. The powders were mixed and then 50 parts of Ludox HS-40 colloidal silica was added along with 12 parts of a 50% caustic/water solution and 76 parts of water. Mixing was done to ensure uniformity of the mull mix and then the sample was extruded through a 1/16"" cylindrical die plate. The material was dried and then ammonium nitrate exchanged to reduce the sodium level, introduced with the caustic, to less than 500 ppm. After exchange, the catalyst was nitrogen pre-calcined at 900° F. for 3 hours and then air was slowly introduced and the catalyst was burned free of carbon at 1000° F. for 6 hours. Steam was then introduced at 1000° F. for 4 hours.

Alumina Bound ZSM-5 Catalyst

A comparative alumina bound catalyst was formulated by the following procedure: 250 parts of a small crystal ZSM-5 (0.02–0.05 micron size) drycake was added to a muller mixer along with 164 parts of psuedoboehmite alumina. The powder was mixed and then 238 parts of water was added. Mixing was done to ensure uniformity of the mull mix and then the sample was extruded through a 1/16"" cylindrical die plate. The material was dried and then the catalyst was nitrogen pre-calcined at 900° F. for 3 hours and then air was slowly introduced and the catalyst was burned free of carbon at 1000° F. for 6 hours. Steam was then introduced at 1000° F. for 4 hours.

Determination of Crystal Size

The crystal size of the ZSM-5 is measured to be small crystal (0.02 to 0.05 micron) by the use of Transmission Electron Microscopy (TEM).

Determination of Diffusion Barrier, $D/r^2$

By selecting appropriate probe molecules with known molecular dimensions (in the range of ~4 to 10 angstroms), it is possible to investigate shapes and sizes of pore openings in molecular sieves. From among linear, branched, and cyclic paraffins, as well as substituted benzene, molecules are selected to probe small, intermediate, and large-pore zeolites. Data are collected using a TA 2950 TGA. About 30 mg are loaded into the TGA. After pretreating in helium at 500° C., the sample is cooled to sorption temperature, e.g., 120° C. for 2,2-Dimethylbutane, and the hydrocarbon is introduced. The raw data obtained are weight vs. time. In addition to total hydrocarbon sorption capacity, uptake rates are also obtained from the linear portion of the initial uptake vs. square root of time plot. Using the Crank equation [Crank, "The Mathematics of Diffusion", Oxford University Press, Ely House, London, 1957] for flat plate geometry, the following equation is derived for ZSM-5:

$$D/r^2\ (\times 10^{-6})=40834.5\times(S/Q)^2$$

where S is the slope and Q is the capacity for n-$C_6$. The constant is calculated by replacing the equilibrium capacity for 2,2-Dimethylbutane with the ratio of capacities of 2,2-Dimethylbutane to $nC_6$ for a pure material.

Example 2

Pilot Plant Testing

The catalyst in Example 1 was employed for the alkylation of benzene with ethylene under conditions comprising an ethylene WHSV of from 2 to 4 $hr^{-1}$, benzene to ethylene weight ratio of 50, pressure of 250 psig, and temperature of from 730° to 780° F. The catalyst was tested in a simulation of a top catalyst bed in a 4 to 6 bed reactor.

Figure 1:
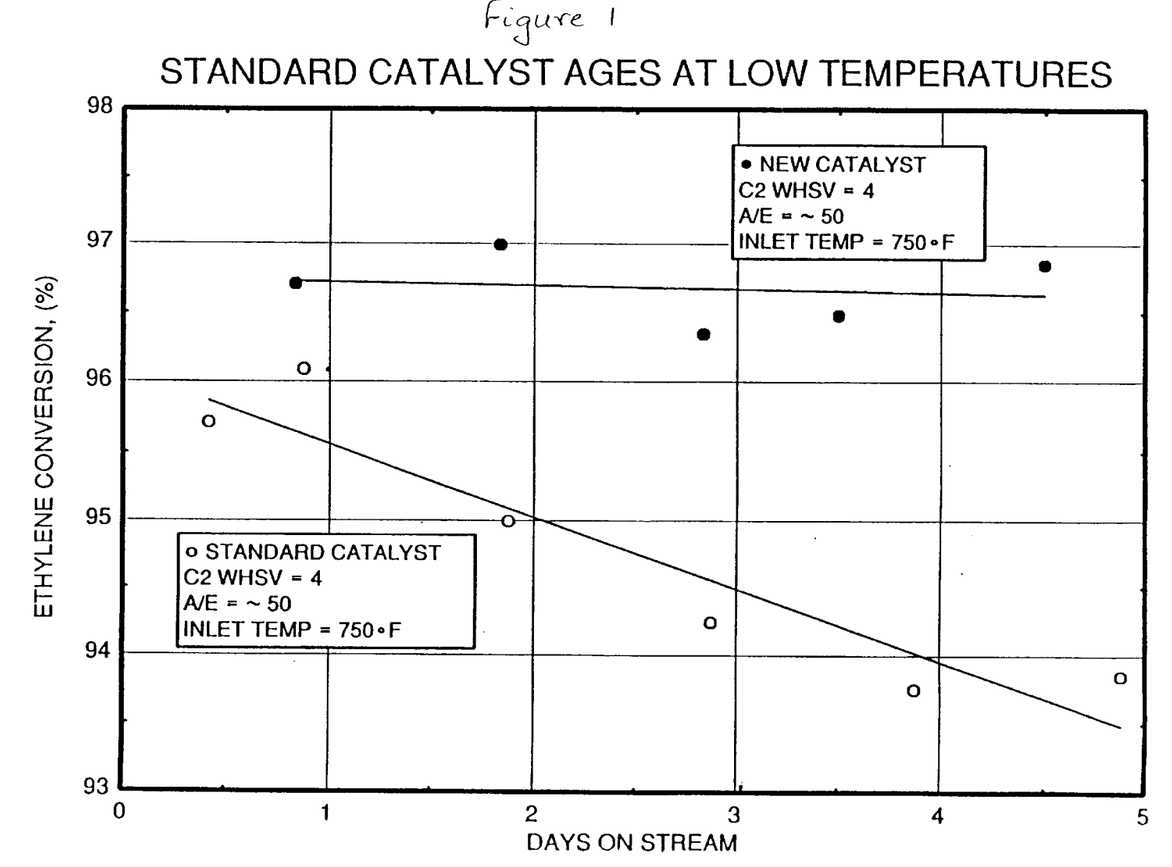
FIG. 1 compares catalyst aging during ethylbenzene production (% ethylene conversion over days on stream) for a silica-bound catalyst of the present invention and a conventional alumina-bound catalyst.

As shown in FIG. 1, catalyst stability for the silica-bound catalyst was greater than that of the comparative alumina-bound catalyst at inlet temperatures of 750° F. as measured by ethylene conversion over days on stream at an ethylene WHSV of 4, aromatic/ethylene weight ratio of about 50.

Figure 2:
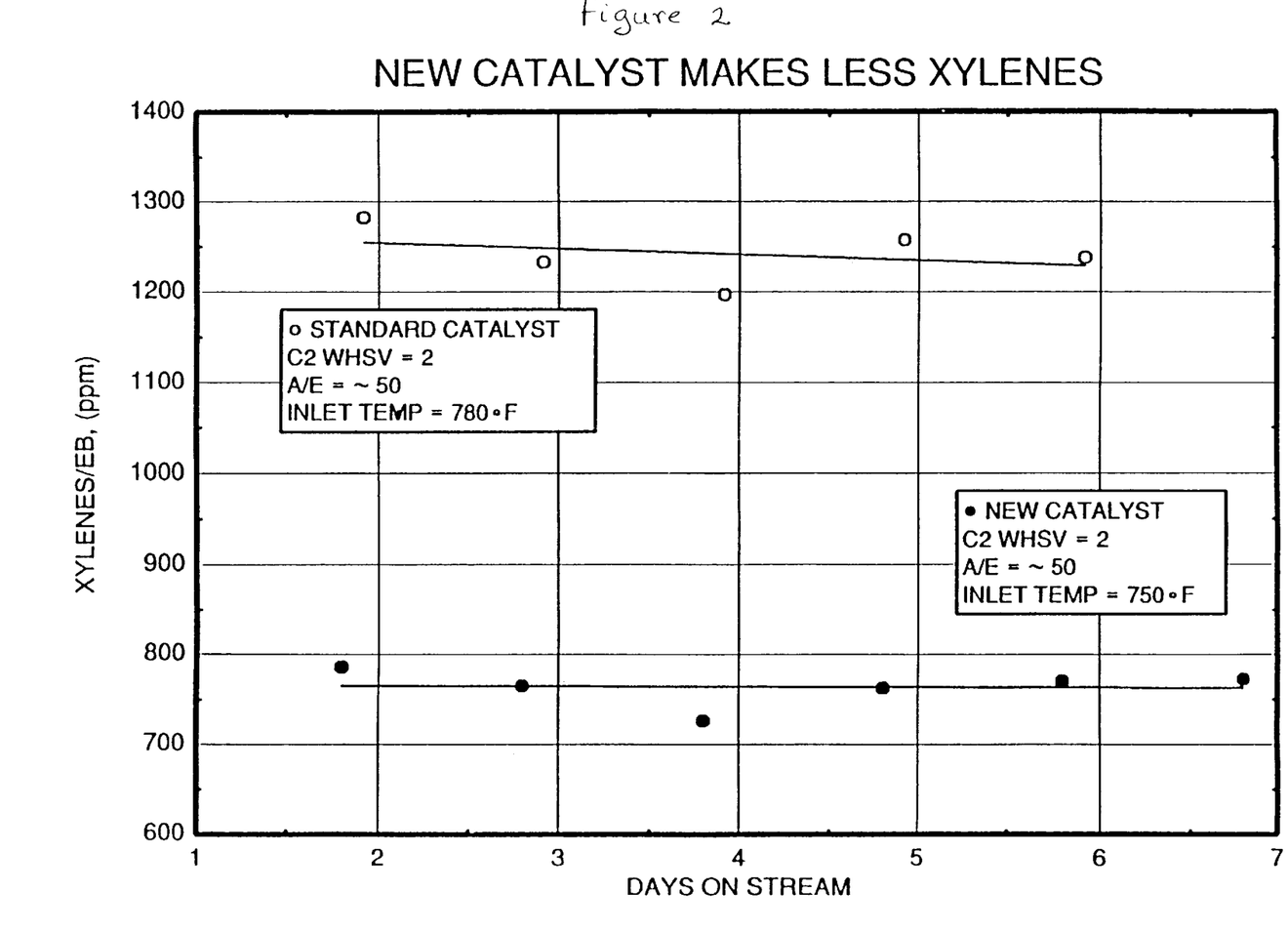
FIG. 2 compares xylene make during ethylbenzene production (% ethylene conversion over days on stream) for a silica-bound catalyst of the present invention and a conventional alumina bound catalyst.

Xylenes make for the two catalysts were compared at operating conditions that offer stable operation, i.e., 750° F. for the silica-bound catalyst and 780° F. for the alumina-bound catalyst. FIG. 2 shows a significant reduction in xylene make for the new catalyst.

Figure 3:
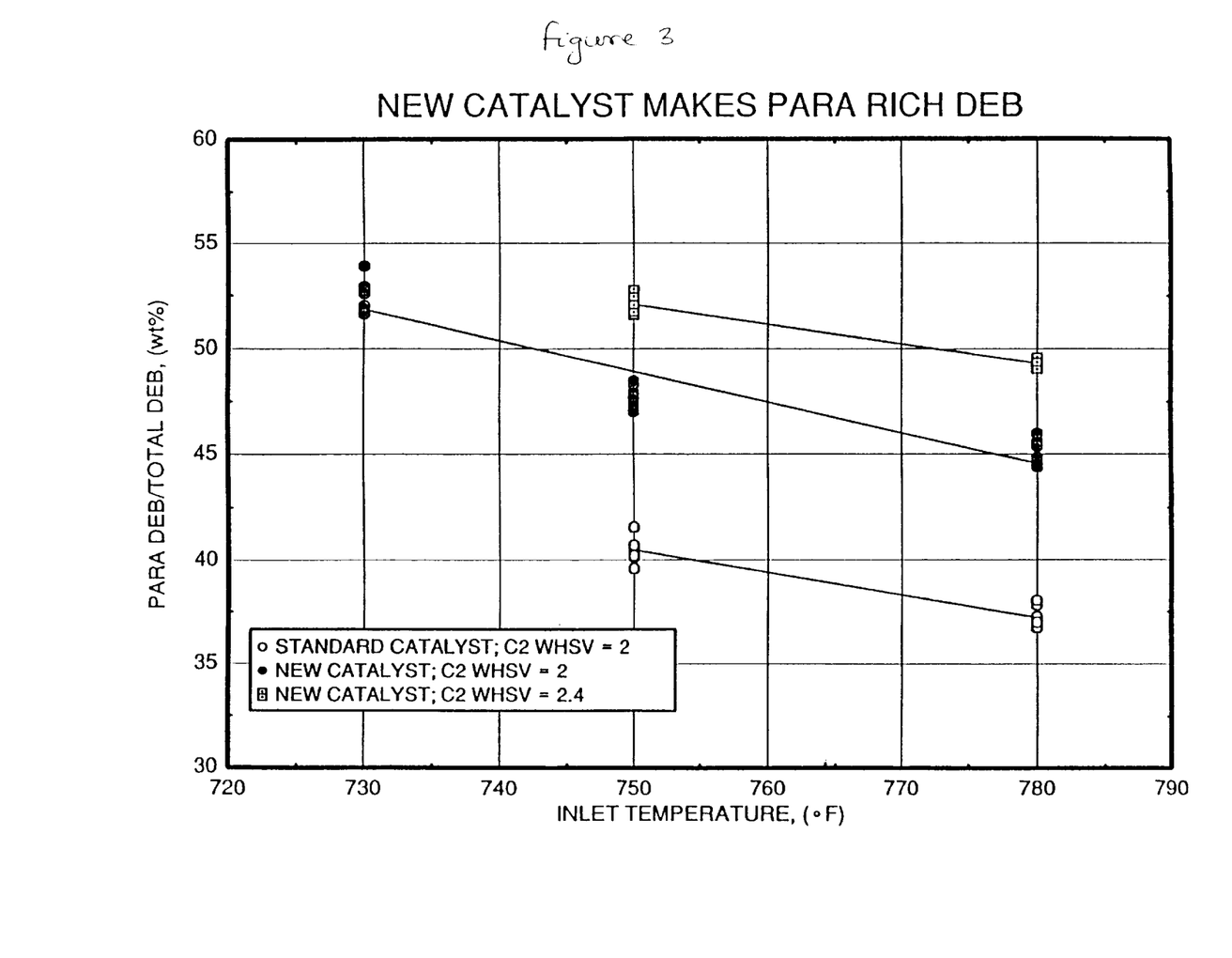
FIG. 3 compares para-diethylbenzene/total diethylbenzene versus inlet temperature (° F.) for a silica-bound catalyst of the present invention and a conventional alumina bound catalyst.

Diethylbenzene (DEB) make from the alkylating reactor is the major by-product of ethylbenzene production. The DEBs are reacted with benzene to be converted back to ethylbenzene in a transalkylating reactor. FIG. 3 depicts a significant increase in para-diethylbenzene/total DEB for the present invention at varying inlet temperatures compared to the alumina-bound catalyst. para-Diethylbenzene is more readily converted back to ethylbenzene by transalkylation. The catalysts are tested under comparable conditions (ethylene WHSV of 2, benzene/ethylene weight ratio of about 50 and inlet temperatures of 730–780° F. for silica-bound and 750°–780° F. for alumina-bound catalysts). Data are also provided for silica-bound catalyst at WHSV of 2.4.

Figure 4:
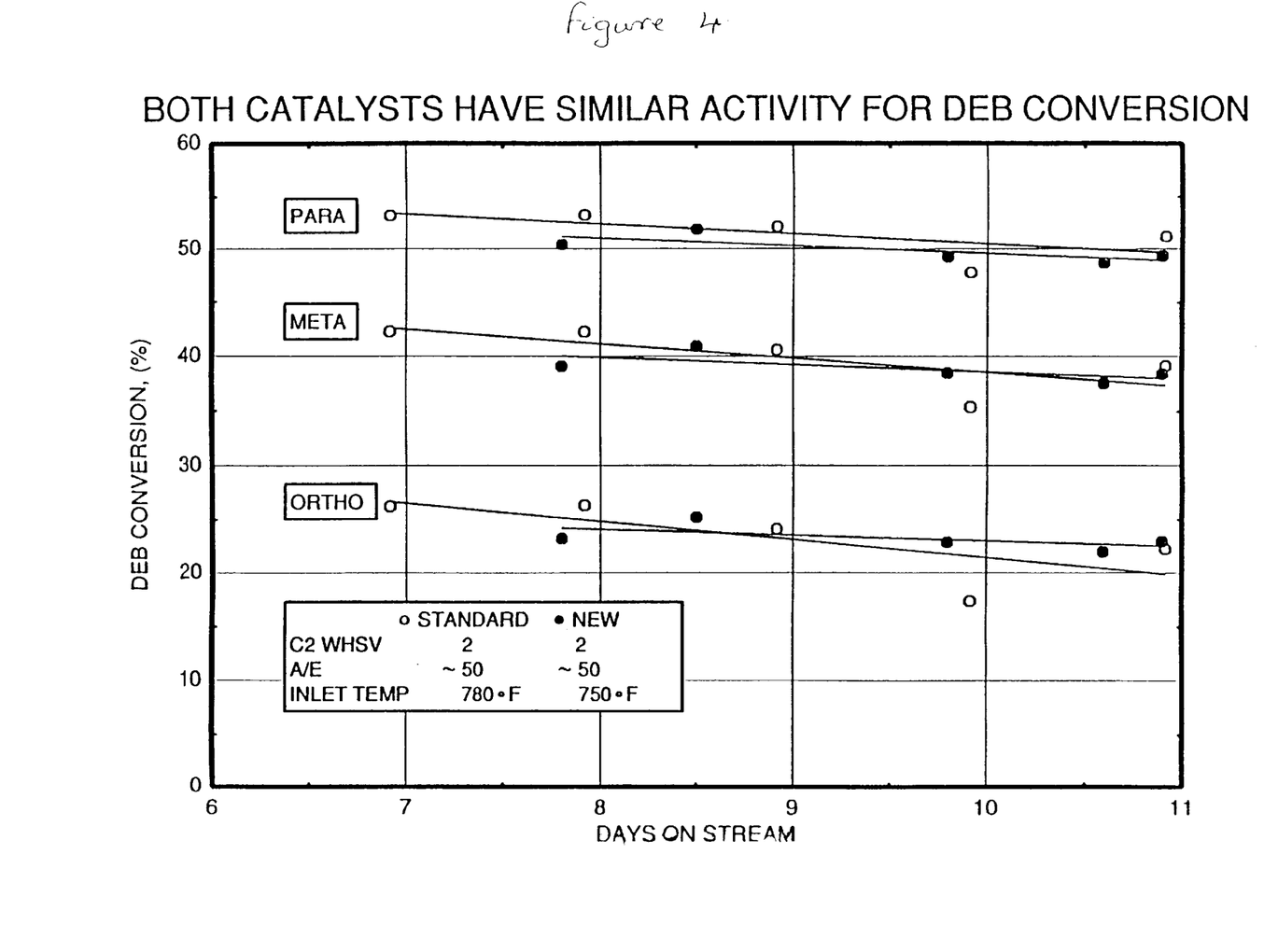
FIG. 4 compares similar diethylbenzene conversions versus days on stream for a silica-bound catalyst of the present invention and a conventional alumina-bound catalyst.

DEB conversion for both catalysts indicated similar activity for DEB conversion as depicted in FIG. 4 under comparable conditions (ethylene WHSV of 2, benzene/ethylene weight ratio of about 50 and inlet temperatures of 750° F. for silica-bound and 780° F. for alumina-bound catalysts). Thus the silica bound catalyst can be useful in both polyalkylating and transalkylating reactions.

What we claim is:

1. A process for alkylating aromatics which comprises contacting an aromatic-containing feed with alkylating agent in the presence of a silica-bound ZSM-5 zeolite catalyst containing at least 70 wt. % zeolite, wherein the ZSM-5 has a crystal size no greater than 0.05 micron, and said catalyst has a Diffusion Parameter, $D/r^2$, for 2,2-dimethylbutane of at least 500, when measured at a temperature of 120° C. and a 2,2-dimethylbutane pressure of 60 torr (8 kPa), said contacting being conducted under alkylating conditions to provide a product containing a monoalkylated aromatic fraction and a polyalkylated aromatic fraction, wherein the polyalkylated aromatic fraction contains at least 40 wt. % of the para-dialkylaromatic species.

2. The process of claim 1 wherein said zeolite has a $SiO_2/Al_2O_3$ molar ratio of greater than 40, and a crystal size of 0.02 to 0.05 micron.

3. The process of claim 1 wherein said catalyst contains from 70–90 wt. % zeolite and said zeolite has a $SiO_2/Al_2O_3$ molar ratio ranging from about 60 to about 80.

4. The process of claim 1 wherein said catalyst contains 75–85 wt. % zeolite and said zeolite has a $SiO_2/Al_2O_3$ molar ratio of about 70.

5. The process of claim 1 wherein said aromatic-containing feed comprises benzene, said alkylating agent comprises ethylene and said para-dialkylaromatic is para-diethylbenzene.

6. The process of claim 5 wherein said alkylating conditions include a temperature of from about 650 to 900° F. (343 to 482° C.), a pressure of about atmospheric to about 3000 psig, a WHSV based on ethylene of from about 0.5 to about 10.0 $hr^{-1}$ and a mole ratio of benzene to ethylene of from 1:1 to 30:1.

7. The process of claim 5 which provides ethylene conversion of at least 96 wt. % ethylene conversion after 4 days on stream at ethylene WHSV of 4, aromatics/ethylene weight ratio feed of 50 and inlet temperature of 750° F.; and makes para-diethylbenzene/total diethylbenzene greater than 45 wt. % at ethylene WHSV of 2, aromatics/ethylene weight ratio feed of 50 and inlet temperature of 750° F.

8. The process of claim 1 wherein said catalyst has a Diffusion Parameter, $D/r^2$, for 2,2-dimethylbutane of 700 to 2000, when measured at a temperature of 120° C. and a 2,2-dimethylbutane pressure of 60 torr (8 kPa).

9. The process of claim 1 wherein said polyalkylated aromatic fraction contains at least 45 wt. % of the para-dialkylaromatic species.

10. A process for preparing a monoalkylated aromatic compound which comprises:
i) contacting an aromatic-containing feed in an alkylating reactor with alkylating agent in the presence of a silica-bound ZSM-5 zeolite alkylation catalyst containing at least 70 wt. % zeolite, wherein the ZSM-5 has a crystal size no greater than 0.05 micron, and said catalyst has a Diffusion Parameter, $D/r^2$, for 2,2-dimethylbutane of at least 500, when measured at a temperature of 120° C. and a 2,2-dimethylbutane pressure of 60 torr (8 kPa), said contacting being conducted under alkylating conditions to provide a product containing a monoalkylated aromatic fraction and a polyalkylated aromatic fraction, wherein the polyalkylated aromatic fraction contains at least 40 wt. % of the para-dialkylaromatic species;
ii) separating the polyalkylated aromatic fraction from the product, and
iii) contacting the polyalkylated aromatic fraction in the presence of unsubstituted aromatic and a transalkylation catalyst under transalkylating conditions to provide a mono-alkylated aromatic-rich stream.

11. The process of claim 10 wherein said zeolite has a $SiO_2/Al_2O_3$ molar ratio ranging from 60 to 80 and a crystal size of 0.02 to 0.05 micron.

12. The process of claim 10 wherein step iii) is carried out in a transalkylating reactor separate from said alkylating reactor.

13. The process of claim 10 wherein step iii) is carried out by recycling said para-dialkylaromatic-rich stream to said alkylating reactor.

14. The process of claim 10 wherein said transalkylation catalyst is a silica-bound ZSM-5 zeolite catalyst composite having a crystal size no greater than 0.05 micron.

15. The process of claim 10 wherein said mono-alkylated aromatic comprises ethylbenzene, said aromatic-containing feed comprises benzene, said alkylating agent comprises ethylene and said para-dialkylaromatic is para-diethylbenzene.

16. The process of claim 15 wherein said alkylating conditions include a temperature of from about 650 to 900° F. (343 to 482° C.), a pressure of about atmospheric to about 3000 psig, a WHSV based on ethylene of from about 0.5 to about 2.0 $hr^{-1}$ and a mole ratio of benzene to ethylene of from 1:1 to 30:1.

17. process of claim 15 which provides ethylene conversion of at least 96 wt. %, and less than 800 ppm xylenes/EB, after 4 days on stream at ethylene WHSV of 4, aromatics/ethylene weight ratio feed of 50 and inlet temperature of 750° F.; and provides para-diethylbenzene/total diethylbenzene at greater than 45 wt. % at ethylene WHSV of 2 aromatics/ethylene weight ratio feed of 50 and inlet temperature of 750° F.

18. The process of claim 15 wherein said ethylbenzene-rich stream contains no greater than 0.6 wt. % of $C_{11+}$ residue.

19. A process for preparing a monoalkylated aromatic compound which comprises:
i) contacting an aromatic-containing feed in an alkylating reactor with alkylating agent in the presence of a silica-bound ZSM-5 zeolite alkylation catalyst cntaining at least 70 wt. % zeolite, wherein the ZSM-5 has a crystal size no greater than 0.05 micron, and said catalyst has a Diffusion Parameter, $D/r^2$, for 2,2-dimethylbutane of at least 500, when measured at a temperature of 120° C. and a 2,2-dimethylbutane pressure of 60 torr (8 kPa), said contacting being conducted under alkylating conditions to provide a product containing a monoalkylated aromatic fraction and a polyalkylated aromatic fraction, wherein the polyalkylated aromatic fraction contains at least 40 wt. % of the para-dialkylaromatic species;

ii) separating the polyalkylated aromatic fraction from the product, and iii) contacting the polyalkylated aromatic fraction in the presence of unsubstituted aromatic and a transalkylation catalyst comprising a silica-bound ZSM-5 zeolite catalyst composite having a crystal size no greater than 0.05 micron, under transalkylating conditions to provide a mono-alkylated aromatic-rich stream.

20. The process of claim 19 wherein said transalkylation catalyst is a silica-bound ZSM-5 zeolite catalyst containing at least 70 wt % zeolite, said transalkylation catalyst having a Diffusion Parameter, $D/r^2$, for 2,2-dimethylbutane of at least 500, when measured at a temperature of 120° C. and a 2,2-dimethylbutane pressure of 60 torr (8 kPa).

* * * * *

UNITED STATES PATENT AND TRADEMARK OFFICE
CERTIFICATE OF CORRECTION

PATENT NO.        : 6,670,517 B1  
APPLICATION NO. : 09/644999  
DATED             : December 30, 2003  
INVENTOR(S)       : Abichandani et al.

Page 1 of 1

It is certified that error appears in the above-identified patent and that said Letters Patent is hereby corrected as shown below:

Claim 1, col. 9, line 22, "$D/r^2$" should read -- $D/(r^2 \times 10^6)$ --.

Claim 8, col. 9, line 57, "$D/r^2$" should read -- $D/(r^2 \times 10^6)$ --.

Signed and Sealed this

Eighth Day of December, 2009

David J. Kappos  
*Director of the United States Patent and Trademark Office*